United States Patent
Hashimoto

(10) Patent No.: US 8,430,820 B2
(45) Date of Patent: Apr. 30, 2013

(54) ULTRASONIC IMAGING APPARATUS

(75) Inventor: Hiroshi Hashimoto, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 921 days.

(21) Appl. No.: 12/253,632

(22) Filed: Oct. 17, 2008

(65) Prior Publication Data

US 2009/0105595 A1    Apr. 23, 2009

(30) Foreign Application Priority Data

Oct. 18, 2007  (JP) .................................. 2007-271478

(51) Int. Cl.
    *A61B 8/00*    (2006.01)
(52) U.S. Cl.
    USPC ........... 600/458; 600/437; 600/407; 600/420; 600/431
(58) Field of Classification Search .................. 600/437, 600/420, 431, 458
    See application file for complete search history.

(56) References Cited

U.S. PATENT DOCUMENTS

| | | | |
|---|---|---|---|
| 5,459,769 A | 10/1995 | Brown | |
| 5,469,849 A | 11/1995 | Sasaki et al. | |
| 5,935,069 A | 8/1999 | Chandler et al. | |
| 5,944,666 A | 8/1999 | Hossack et al. | |
| 5,971,928 A | 10/1999 | Dodd et al. | |
| 6,245,019 B1 | 6/2001 | Kamiyama | |
| 6,461,300 B2 | 10/2002 | Hashimoto et al. | |
| 6,503,203 B1 | 1/2003 | Rafter et al. | |
| 6,505,064 B1 * | 1/2003 | Liu et al. ....................... | 600/420 |
| 6,786,869 B2 | 9/2004 | Hashimoto | |
| 7,221,972 B2 | 5/2007 | Jackson et al. | |
| 2004/0120559 A1 | 6/2004 | Hall | |
| 2006/0020209 A1 | 1/2006 | Hashimoto | |

* cited by examiner

*Primary Examiner* — Unsu Jung
*Assistant Examiner* — Rajeev Siripurapu
(74) *Attorney, Agent, or Firm* — Armstrong Teasdale LLP

(57) ABSTRACT

An ultrasonic imaging apparatus which acquires tomographic image information of a subject to which a contrast agent is administered, and displays the tomographic image information, includes an administration time timer which is started up while the acquisition is being performed and which measures a time that elapses from a time of the start-up to which a predetermined offset time is added, and an offset time setting device which sets the offset time to the administration time timer when the start-up is performed.

20 Claims, 10 Drawing Sheets

FIG. 3

| SUBJECT INFORMATION | OPERATION TIME INFORMATION ||
| --- | --- | --- |
| | STOP TIME INFORMATION | ELAPSED TIME INFORMATION |
| TARO KIMURA | 10:30 | 10 |
| HANAKO SUZUKI | 11:00 | 10 |
| . . . . | . . . . | . . . . |

ULTRASONIC IMAGING APPARATUS

CROSS REFERENCE TO RELATED APPLICATIONS

This application claims the benefit of Japanese Patent Application No. 2007-271478 filed Oct. 18, 2007, which is hereby incorporated by reference in its entirety.

BACKGROUND OF THE INVENTION

The subject matter disclosed herein relates to an ultrasonic imaging apparatus which acquires tomographic image of a subject to which a contrast agent is administered.

In an ultrasonic imaging apparatus, examinations using contrast agents are frequently performed. The contrast agents administered to a subject circulate in the blood and permeate through within a tissue. These contrast agents are projected as high brightness areas in the case of a tomographic image acquired from the ultrasonic imaging apparatus and yield information useful clinically.

The contrast agents are made up of micro bubbles of a few μm or so. A plurality of types different in property exist as the contrast agents. An initially-developed contrast agent (Levovist) has destroyed bubbles by applying ultrasound of high MI (Mechanical Index) and effected imaging on strong reflected ultrasound developed upon destruction thereof. This contrast agent is observed on a tomographic image only at the instant when ultrasound of high sound pressure is applied. Thereafter, the contrast agent loses a contrast function.

On the other hand, there has recently been developed a contrast agent (Sonazoid) that does not destroy bubbles and maintains a contrast function even though low MI ultrasound is applied repeatedly. In the present contrast agent, the manner in which the contras agent lying within a subject changes with time, can be repeatedly projected and observed on a tomographic image displayed in real time, by once-contrast agent administration.

The contrast agent has the property of being englutted through Kupffer cells of a tissue portion from within the blood vessels. It has also been practiced to observe the contrast agent that permeates into the tissue portion. In the present observation, progress is observed over a long period of time as compared with the case in which the contrast agent migrates into the blood vessels.

In this long-duration examination, it is practiced to locate a treatment chamber for administering the contrast agent to the subject and an examination chamber for imaging the subject in different positions respectively and observe a contrast agent permeation process partly at pivotal points segmented in terms of time. In this case, an operator repeatedly performs a similar examination on the same subject during a plurality of inspection or examination times segmented in terms of time, using an ultrasonic imaging apparatus. The operator also performs other examinations during intervals between the examination times to enhance the availability of the ultrasonic imaging apparatus.

Here, the time that elapses since the administration of the contrast agent to the subject has an important meaning clinically upon the contrast agent examination. Therefore, a timer started up upon administration of the contrast agent exists in the ultrasonic imaging apparatus to measure the above-described elapsed time.

However, it was not easy to control or manage the time that elapses from the administration of the contrast agent to the subject. That is, when the treatment chamber for administering the contrast agent and the examination chamber for imaging the subject are different from each other, the subject is carried or conveyed to the examination chamber after the contrast agent has been administered to the subject in the treatment chamber, and the start-up of the timer for measuring or counting the elapsed time of the contrast agent is performed with respect to the ultrasonic imaging apparatus in the examination chamber. Since the time at which the contrast agent is administered to the subject, and the time taken to start up the timer are different from each other in this case, the elapsed time does not indicate the time that elapses immediately after the administration of the contrast agent to the subject.

When the process of permeation of the contrast agent into the subject is observed partly at the pivotal points segmented in terms of time, there exists a case in which contrast agent examinations for plural subjects are performed on a simultaneous promotion basis using one ultrasonic imaging apparatus. In this case, the ultrasonic imaging apparatus needs to simultaneously manage elapsed times subsequent to the start of administration to the plural subjects. However, this puts a large burden on the operator. It is not easy to put into practice. Although it is also considered that a plurality of timers are provided in the ultrasonic imaging apparatus, it is not efficient if it is considered that the number of timers required upon imaging is only one.

In terms of these, it is of importance of how an ultrasonic imaging apparatus capable of reducing a burden imposed on an operator and measuring an elapsed time from the administration of a contrast agent to a subject without fail even when a contrast agent examination has a complex process, is realized.

BRIEF DESCRIPTION OF THE INVENTION

It is desirable that the problems described previously are solved.

An ultrasonic imaging apparatus according to the invention of a first aspect includes an ultrasonic imaging apparatus which acquires tomographic image information of a subject to which a contrast agent is administered, and displays the tomographic image information, including an administration time timer which is started up while the acquisition is being performed and which measures a time that elapses from a time of the start-up to which a predetermined offset time is added, and an offset time setting device which sets the offset time to the administration time timer when the start-up is performed.

In the invention according to the first aspect, the administration time timer started up when acquisition is started, measures an elapsed time from the time of a start-up with an offset time overlaid thereon. The offset time setting device sets the offset time to the administration time timer.

An ultrasonic imaging apparatus according to the invention of a second aspect is provided wherein in the ultrasonic imaging apparatus described in the first aspect, the offset time is a time from a time at which the administration is performed, to the execution of the start-up.

In the invention of the second aspect, an elapsed time is set as a time from the administration of a contrast agent.

An ultrasonic imaging apparatus according to the invention of a third aspect is provided wherein in the ultrasonic imaging apparatus described in the second aspect, there are provided a timer start key for starting up the administration time timer and a timer stop key for stopping the started-up administration time timer.

In the invention of the third aspect, the administration time timer measures an elapsed time from after the administration of a contrast agent even though it is repeatedly turned ON/OFF.

An ultrasonic imaging apparatus according to the invention of a fourth aspect is provided wherein in the ultrasonic imaging apparatus described in any one of the first through third aspects, the offset time setting device includes a manual time setting device which inputs offset time information indicative of the offset time manually.

In the invention of the fourth aspect, the manual time setting device sets offset time information to a value that an operator desires.

An ultrasonic imaging apparatus according to the invention of a fifth aspect is provided wherein in the ultrasonic imaging apparatus described in the fourth aspect, there is provided an administration time input part which inputs administration time information at which the administration is performed, and the manual time setting device calculates the offset time, based on the administration time information.

In the invention of the fifth aspect, an offset time is determined from manually-inputted administration time information.

An ultrasonic imaging apparatus according to the invention of a sixth aspect is provided wherein in the ultrasonic imaging apparatus described in any one of the first through fifth aspects, the offset time setting device includes automatic time setting device which inputs the offset time information indicative of the offset time automatically.

In the invention of the sixth aspect, an offset time is inputted automatically.

An ultrasonic imaging apparatus according to the invention of a seventh aspect is provided wherein in the ultrasonic imaging apparatus described in the sixth aspect, the automatic time setting device includes an image memory unit which, when the administration time timer is stopped, stores subject information for identifying the subject and operation history time information having operated the administration time timer in association with the subject information as header information of the tomographic image information along with the tomographic image information.

In the invention of the seventh aspect, automatic time setting device stores operation history time information of an administration time timer along with tomographic image information.

An ultrasonic imaging apparatus according to the invention of an eighth aspect is provided wherein in the ultrasonic imaging apparatus described in the sixth aspect, the automatic time setting device includes an operation history memory unit which, when the administration time timer is stopped, stores subject information for identifying the subject and operation history time information having operated or activated the administration time timer in association with the subject information.

In the invention of the eighth aspect, automatic time setting device stores operation history time information of an administration time timer in an operation history memory unit.

An ultrasonic imaging apparatus according to the invention of a ninth aspect is provided wherein in the ultrasonic imaging apparatus described in the seventh or eighth aspect, the automatic time setting device includes an operation history determination device which determines whether subject information of the subject on which the acquisition is performed exists in the image memory unit or the operation history memory unit upon execution of the start-up.

In the invention of the ninth aspect, operation history determination device determines whether a contrast agent examination for a subject has been performed in the past.

An ultrasonic imaging apparatus according to the invention of a tenth aspect is provided wherein in the ultrasonic imaging apparatus described in the ninth aspect, the operation history determination device sets the offset time to zero when the subject information of the subject is nonexistent in the image memory unit or the operation history memory unit.

In the invention of the tenth aspect, operation history determination device substitutes zero into an offset time where a contrast agent examination for a subject is of a first time.

An ultrasonic imaging apparatus according to the invention of an eleventh aspect is provided wherein in the ultrasonic imaging apparatus described in the ninth or tenth aspect, the operation history determination device includes an offset calculation device which calculates the offset time, based on the operation history time information associated with the subject information of the operation history memory unit when the subject information of the subject exists in the image memory unit or the operation history memory unit.

In the invention of the eleventh aspect, when a contrast agent examination for a subject has been performed in the past, an offset calculation device sets the time from the time when a contrast agent has been administered in the past, as an offset time.

An ultrasonic imaging apparatus according to the invention of a twelfth aspect is provided wherein in the ultrasonic imaging apparatus described in any one of the eighth through eleventh aspects, the operation history time information includes any two of elapsed time information indicative of the elapsed time, start time information indicative of a start time of the start-up, and stop time information indicative of a stop time of the stop.

In the invention of the twelfth aspect, the time taken to halt or rest each of intermittently-executed contrast agent examinations is determined using operation history time information.

An ultrasonic imaging apparatus according to the invention of a thirteenth aspect is provided wherein in the ultrasonic imaging apparatus described in any one of the first through twelfth aspects, there is provided a display unit which displays the tomographic image information.

An ultrasonic imaging apparatus according to the invention of a fourteenth aspect is provided wherein in the ultrasonic imaging apparatus described in the thirteenth aspect, the display unit includes a timer display part which displays a standard time on a display screen.

In the invention of the fourteenth aspect, the time taken to perform imaging is confirmed by a timer display part.

An ultrasonic imaging apparatus according to the invention of a fifteenth aspect is provided wherein in the ultrasonic imaging apparatus described in the fourteenth aspect, the timer display part displays the elapsed time on the display screen.

In the invention of the fifteenth aspect, an elapsed time from the time at which a contrast agent has been administered is confirmed by a timer display part.

An ultrasonic imaging apparatus according to the invention of a sixteenth aspect is provided wherein in the ultrasonic imaging apparatus described in the fourteenth aspect, the elapsed time is displayed on the display unit when the administration time timer is started up, and is deleted from the display unit when the administration time timer is stopped.

In the invention of the sixteenth aspect, an elapsed time is displayed as needed.

According to the invention, a measured elapsed time of an administration time timer is set as the time from the administration of a contrast agent to a subject even when a contrast agent examination has a complex process as in the case in which contrast agent examinations for the subject are performed intermittently. It is therefore possible to reduce a burden imposed on an operator and measure an error-free administration time.

Further objects and advantages of the present invention will be apparent from the following description of the preferred embodiments of the invention as illustrated in the accompanying drawings.

BRIEF DESCRIPTION OF THE DRAWINGS

FIG. 3 is an explanatory diagram showing one example of subject information stored in an operation history memory unit.

DETAILED DESCRIPTION OF THE INVENTION

Various embodiments of an ultrasonic imaging apparatus according to the invention will be explained below with reference to the accompanying drawings. Incidentally, the invention is not limited thereby.

Figure 1:
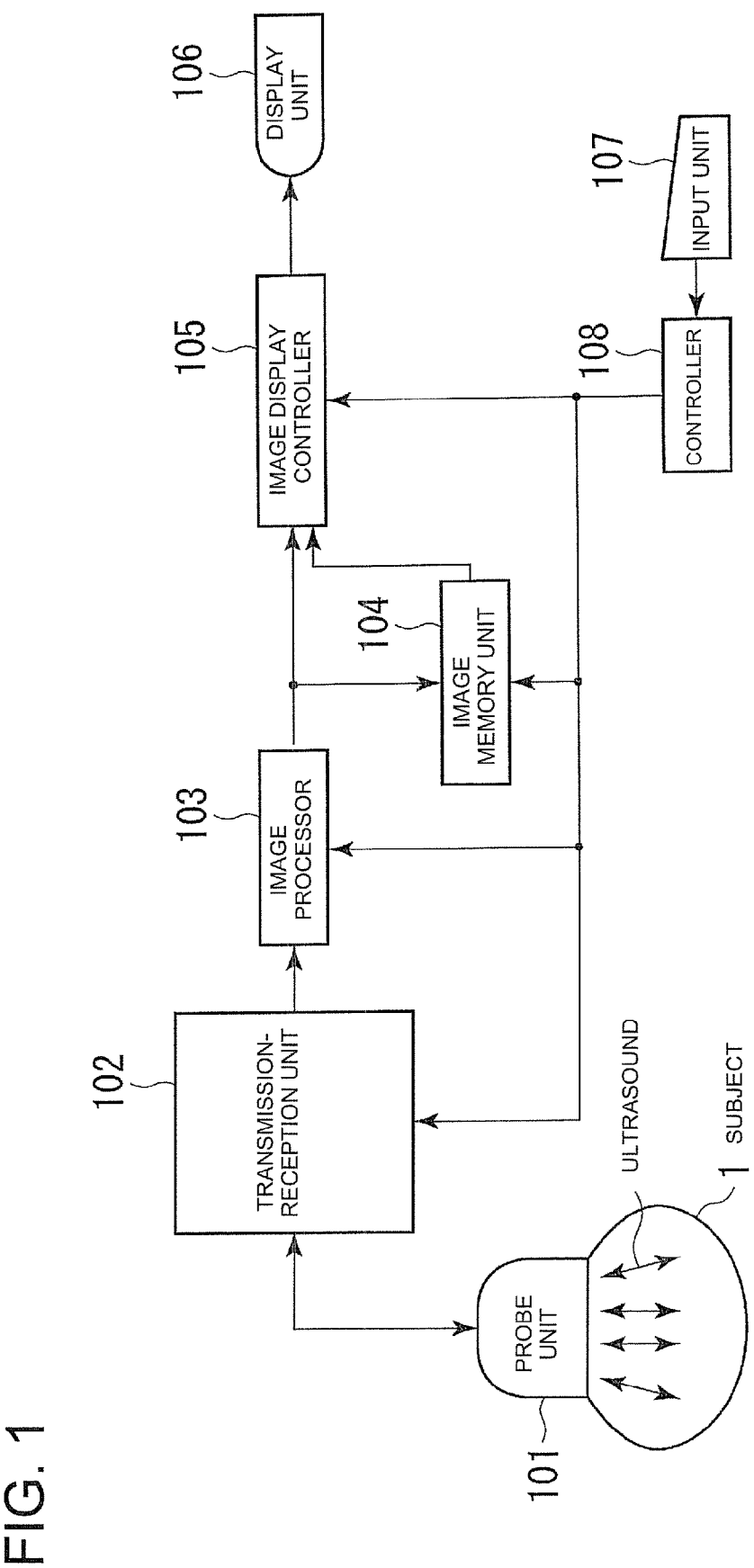
FIG. 1 is a block diagram showing an overall construction of an ultrasonic imaging apparatus.

An overall construction of an ultrasonic imaging apparatus according to the present embodiment will first be described. FIG. 1 is a block diagram showing the overall construction of the ultrasonic imaging apparatus according to the present embodiment. The ultrasonic imaging apparatus has a probe unit 101, a transmission-reception unit 102, an image processor 103, an image memory unit 104, an image display controller 105, a display unit 106, an input unit 107 and a controller 108.

The probe unit 101 repeatedly transmits ultrasound in a specific direction of a portion or region, i.e., a subject 1 for transmitting and receiving the ultrasound and receives ultrasonic signals reflected from inside the subject 1 as time-series sound rays. Concurrently with it, the probe unit 101 performs electronic scanning while the directions to apply the ultrasound are being switched sequentially. Incidentally, although not shown in the figure, piezoelectric elements are arranged in the probe unit 101 in array form.

The transmission-reception part 102 is connected to the probe unit 101 by a coaxial cable and performs the generation of an electric signal for driving each piezoelectric element of the probe unit 101 and first-stage amplification of each ultrasonic signal received thereat.

The image processor 103 performs the extraction of a tomographic image from the corresponding ultrasonic signal amplified by the transmission-reception unit 102. When a contrast agent is administered to the subject 1, the image processor 103 performs contrast mode processing for generating a contrast mode image in real time. As specific contents of processing, there are, for example, delay/addition processing of a received ultrasonic signal, A/D (analog/digital) conversion processing, processing for writing post-conversion digital information into the image memory unit 104 as image information such as B-mode image information, and the like.

The image memory unit 104 is an image memory for storing each B-mode image information or the like generated by the contrast mode processing. The image memory unit 104 stores the B-mode image information that changes in time therein along with standard time information indicative of the date and time. The image display controller 105 performs display frame rate conversion of the B-mode image information generated at the image processor 103, and shape/position control on a displayed image of the B-mode image information. The image display controller 105 also performs display of ROI (region of interest) indicative of a region of interest on the displayed image of the B-mode image information.

The display unit 106 displays information about the display frame rate conversion and the shape/position control on the image display both carried out by the image display controller 105, visually to an operator by using a CRT (cathode ray tube) or an LCD (liquid crystal display) or the like.

The input unit 107 consists of a keyboard and a pointing device or the like. The input unit 107 transmits an operation or control input signal inputted by the operator to the controller 108. The input unit 107 performs the input of, for example, the start and stop of a timer, the setting of the position of an ROI or a pointer or the like positioned on the display image of the display unit 106, and the determination of the ROI position or the designation of the pointer.

The controller 108 controls the operations of the above respective parts of the ultrasonic imaging apparatus, based on the operation input signal supplied from the input unit 107 and the program and data stored in advance to cause the display unit 106 to display the B-mode image or the like.

Figure 2:
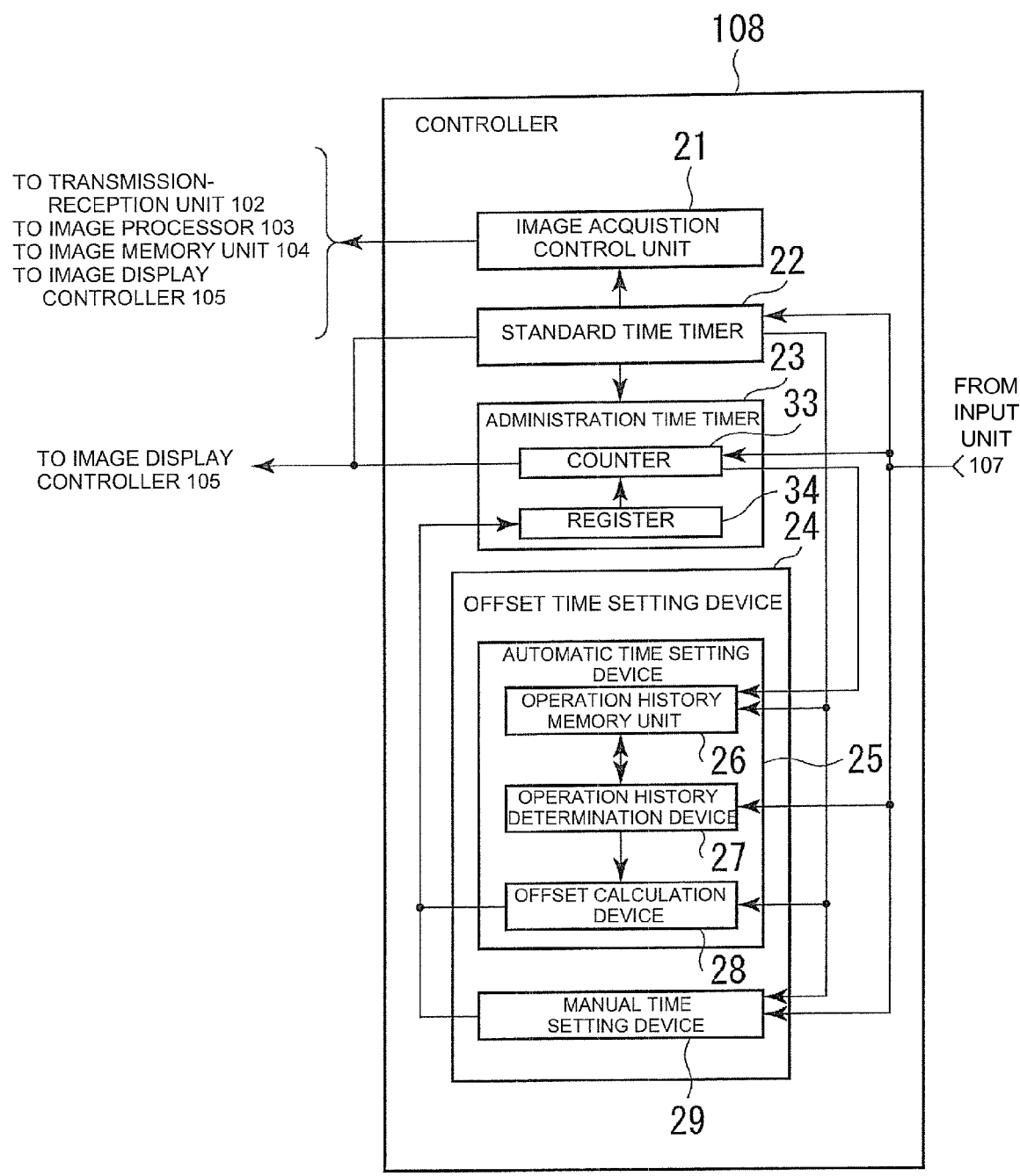
FIG. 2 is a function block diagram illustrating a functional construction of a controller according to an embodiment.

FIG. 2 is a block diagram showing the construction of the controller 108. The controller 108 includes an image acquisition control unit 21, a standard time timer 22, an administration time timer 23 and an offset time setting device 24. The offset time setting device 24 includes an automatic time setting device 25 and a manual time setting device 29. The automatic time setting device 25 includes an operation history memory unit 26, an operation history determination device 27 and an offset calculation device 28.

The image acquisition control unit 21 performs control on the transmission-reception unit 102, the image processor 103, the image memory unit 104 and the image display controller 105 and performs an ultrasonic scan, based on scan information such as imaging mode information, depth-of-focus or focus depth information and the like inputted from the input unit 107 to acquire tomographic image information such as B-mode image information.

The standard time timer 22 is a counter for counting the standard time, for example, Japanese local standard time in Japan. Time information of the standard time timer 22 is displayed on the display screen. When tomographic image information is stored in the image memory unit 104, standard time information indicative of the date and time at which the tomographic image information is acquired, is attached to a header or the like of the tomographic image information.

The administration time timer 23 includes a counter 33 and a register 34. The counter 33 counts an elapsed time from its start-up, based start-up information inputted from the input unit 107. Information about the elapsed time of the counter 33 is outputted to the image display controller 105 in a manner similar to the standard time timer 22 and displayed on the display unit 106. Incidentally, when the tomographic image information is stored in the image memory unit 104, the elapsed time information is read into the header or the like of the tomographic image information along with stop time information indicative of the time at which the administration time timer 23 stops.

The administration time timer 23 has a register 34 that sets an initial setting time at the start of time measurement by the counter 33 upon starting the measurement of the elapsed time. The time information of the register 34 is loaded into the counter 33 as an initial value. Thereafter, the counter 33 starts the counting of an unillustrated clock and performs the measurement of an elapsed time.

When the contrast agent is administered to the subject 1 before the administration time timer 23 is started, although the value of zero has been set as the initial value, offset time information is inputted to the register 34 by the manual time setting device 29 or the automatic time setting device 25. The offset time information indicates the time between the instant when the contrast agent is administered to the subject 1 and the instant when the administration time timer 23 is started up. The offset time information is set in such a manner that the elapsed time measured by the counter 33 indicates the time that elapses after the administration of the contrast agent.

When the administration time timer 23 is started up, the offset time setting device 24 sets offset time information to the register 34.

The manual time setting device 29 sets offset time information selected from the input unit 107 by the operator and inputted from the input unit 107 by the operator to the register 34.

The automatic time setting device 25 is selected from the input unit 107 by the operator and sets offset time information to the register 34 automatically upon its start-up.

The operation history memory unit 26 is a memory in which the history of the administration time timer 23 started in the past is stored. FIG. 3 is an explanatory diagram showing the contents of history information stored in the operation history memory unit 26. The history information includes subject information at the time that the administration time timer 23 is started, and operation history time information of the administration time timer 23. As the subject information, the name of a subject or a subject ID No. (identification No.) or the like is used. At least two of start time information, stop time information and elapsed time information of the administration time timer 23 are included as the operation history time information.

FIG. 3 has shown as a table, a case including a subject name as subject information, and stop time information and elapsed time information as operation history time information. Since the stop time information and the elapsed time information are associated with the subject information by a link or the like and stored in the operation history memory unit 26, retrieval and reading can be conducted using the subject information.

Here, the stop time information indicates the standard time at which the administration time timer 23 was stopped in the past. The elapsed time information indicates an elapsed time between the instant when the administration time timer 23 was started in the past and the instant when it is stopped subsequently. Incidentally, when the stop information of the administration time timer 23 is inputted from the input unit 107, the subject information and the operation history time information are stored in the operation history memory unit 26.

When the start information of the administration time timer 23 is inputted from the input unit 107, the operation history determination device 27 determines whether the same subject information as the subject information set at the input unit 107 exists in the operation history memory unit 26. When the corresponding subject information exists in the operation history memory unit 26, the operation history determination device 27 reads the stop time information and the elapsed time information and transfers the same to the offset calculation device 28. Incidentally, when the corresponding same subject information exists in the operation history memory unit 26 in plural form, the operation history determination device 27 transfers only stop time information and elapsed time information linked to the latest subject information.

Figure 4:
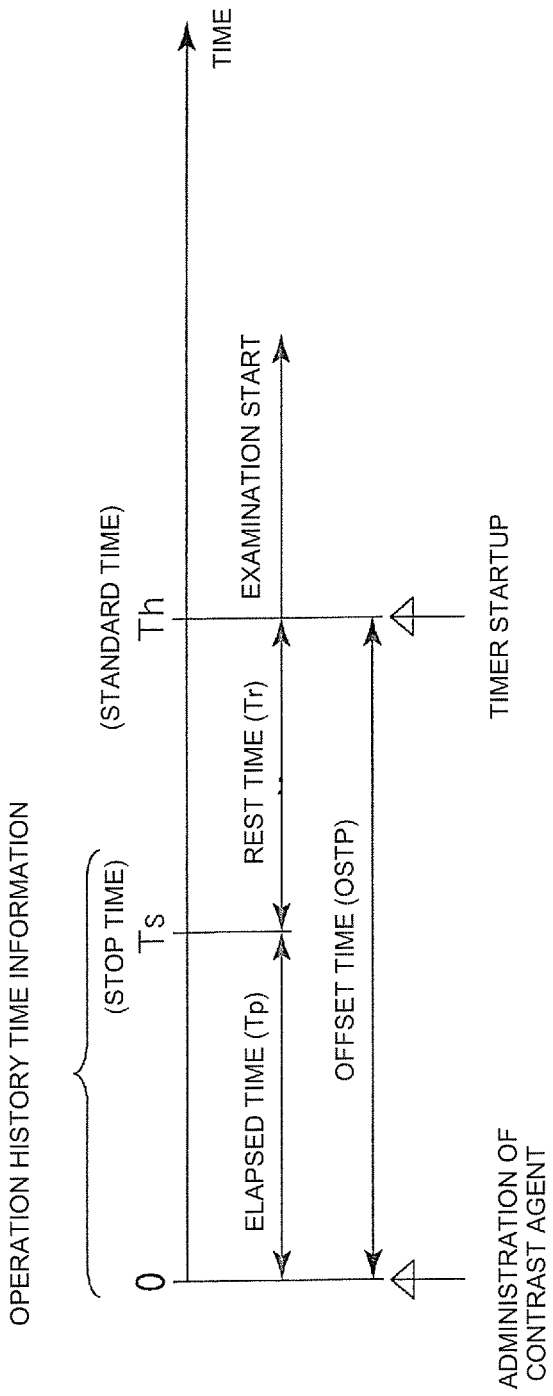
FIG. 4 is an explanatory diagram illustrating a method for calculating an offset time of offset time calculation device.

When the stop time information and elapsed time information of the subject information are transferred from the operation history memory unit 26, the offset calculation device 28 reads the standard time information from the standard time timer 22 and calculates offset time information indicative of the time that has elapsed since the contrast agent has been administered to the subject 1. FIG. 4 is an explanatory diagram typically showing the calculation of an offset time. The horizontal axis indicates the time that will elapse after the administration of the contrast agent to the subject 1. The time taken to start up the administration time timer 23 in order to start a contrast agent examination is illustrated on the time base as a standard time Th. An elapsed time Tp and a stop time Ts that form the operation history time information, which are obtained upon a contrast agent examination performed last time, are illustrated on the left side of the standard time Th. The stop time Ts indicates the standard time at which the administration time timer 23 has been stopped previously, and the elapsed time Tp indicates an elapsed time between the instant when the contrast agent is administered and the instant when the administration time timer 23 was stopped last time.

The calculation of the offset time information is done in the following manner. The stop time Ts is subtracted from the standard time Th read from the standard time timer 22 to obtain a rest time Tr of the administration time timer 23.

$$Tr = Th - Ts$$

The offset calculation device 28 adds the rest time Tr to the elapsed time Tp to calculate an offset time OSTP corresponding to the initial value of the elapsed time.

$$OSTP = Tr + Tp$$

The offset time OSTP indicates the time from the administration of the contrast agent to the subject 1 to the standard time Th at which the contrast agent examination is started. The offset calculation device 28 sets the value of the offset time OSTP to the register 34 as an initial value. When a start signal is inputted, the administration time timer 23 loads the contents of the register 34 into the counter 33 and thereafter starts counting.

Figure 5:
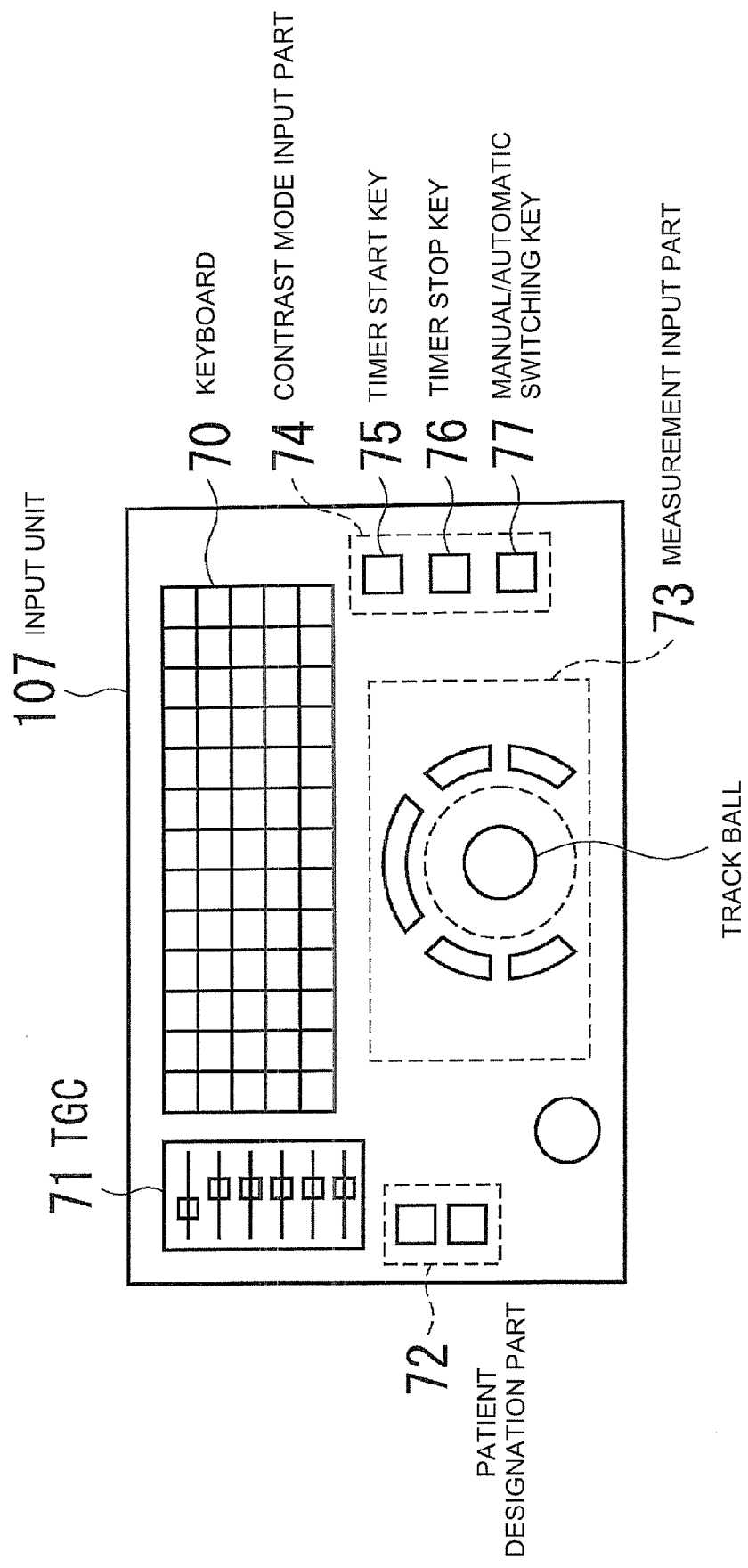
FIG. 5 is a diagram showing one example of an operation panel that constitutes an input unit.

FIG. 5 is a diagram showing one example of the input unit 107. The input unit 107 includes a keyboard 70, a TGC (Time Gain Controller) 71, a patient designation part 72 including a New Patient Key or the like, a measurement input part 73 including a track ball, the setting of an ROI, etc., and a contrast mode input part 74 including setting keys at the use of the contrast agent. The contrast mode input part 74 includes a timer start key 75, a timer stop key 76 and a manual/automatic switching key 77. The timer start key 75 starts up the administration time timer 23 to start counting. The timer stop key 76 stops the counting of the administration time timer 23. The manual/automatic switching key 77 performs switching between the manual and automatic inputs of an offset time.

Figure 6:
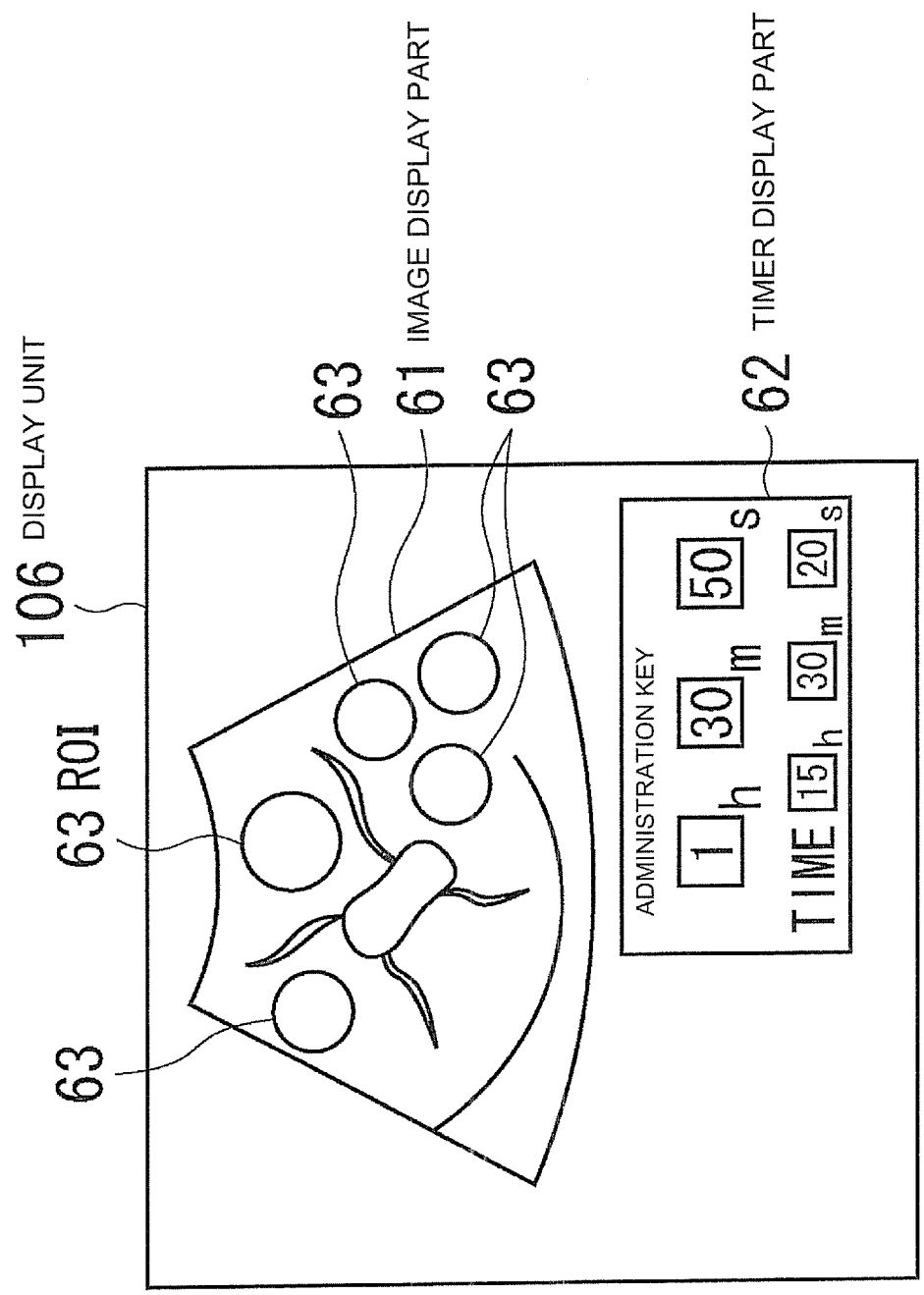
FIG. 6 is an explanatory diagram depicting constituent elements of a display screen displayed on a display unit.

FIG. 6 is one example of the display screen of the display unit 106. The display screen includes an image display part 61 and a timer display part 62. The image display part 61 displays a tomographic image such as a B-mode image. When the contrast agent is administered to the subject 1, the contrast agent is projected or represented as a high brightness area on the tomographic image. The operator sets each ROI 63 indicative of a region of interest to a portion or region to be observed and measures the permeation of the contrast agent from the manner in which the average brightness value or the like of the ROI 63 changes with time. Incidentally, the set region of interest may extend to plural forms.

The timer display part 62 displays the time information of the standard time timer 22 and the administration time timer 23 in real time. The time-of-day information of the standard time timer 22 is displayed below the timer display part 62. The elapsed time information indicated by the counter 33 of the administration time timer 23 is displayed above the timer display part 62. Incidentally, the elapsed time information is displayed simultaneously with the time when the administration time timer 23 is started up. Simultaneously with the time when the administration time timer 23 is stopped, its display is discontinued.

Figure 7:
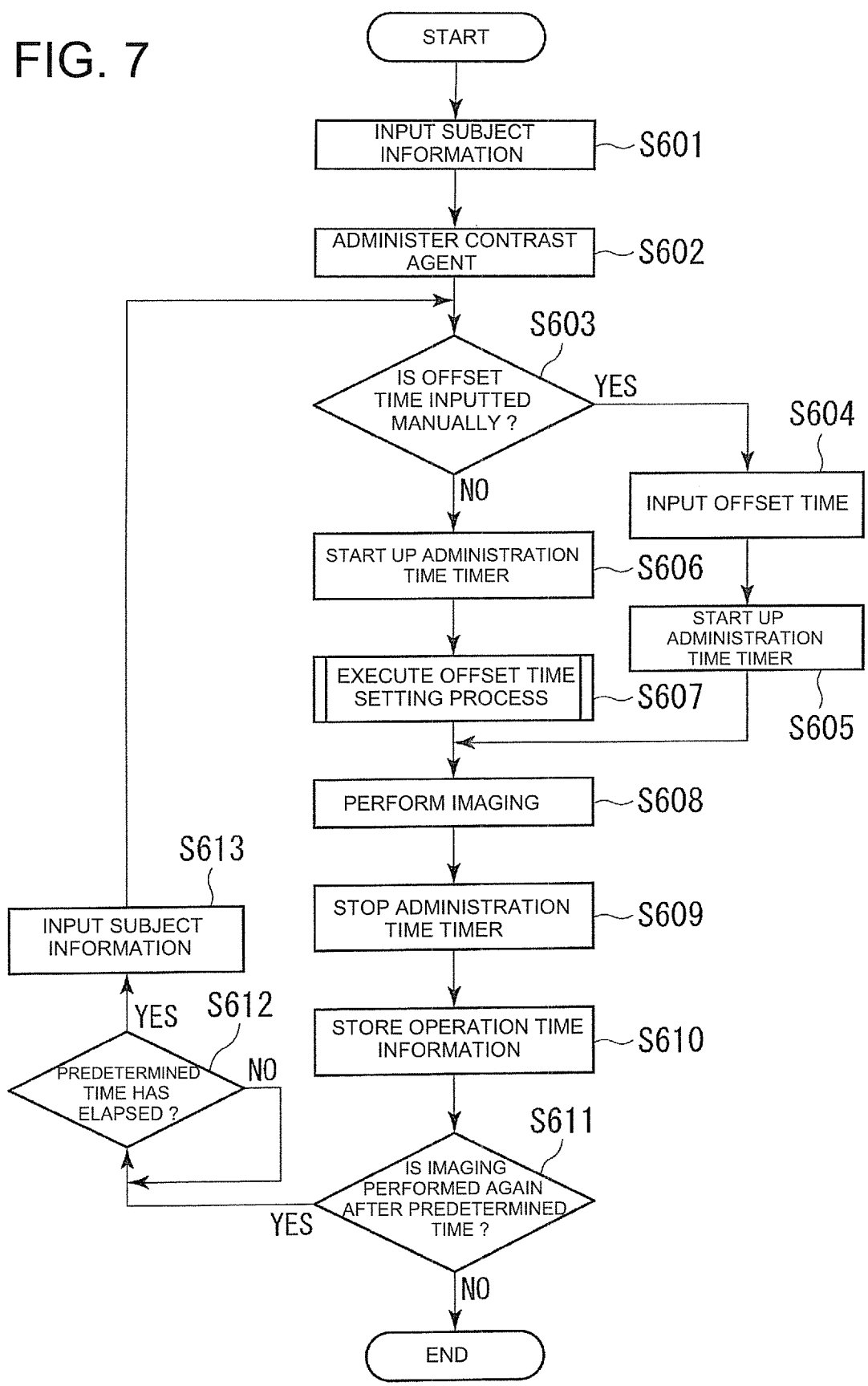
FIG. 7 is a flowchart showing the operation of the ultrasonic imaging apparatus according to the embodiment.

The operation of the ultrasonic imaging apparatus according to the present embodiment will next be explained using FIG. 7. FIG. 7 is a flowchart showing the operation of the ultrasonic imaging apparatus according to the present embodiment. The operator first inputs subject information about the name of a subject 1 or the like through the input unit 107 (Step S601) and administers the contrast agent to the subject 1 (Step S602). This administration is done through an intravenous injection of the contrast agent, for example.

Figure 8:
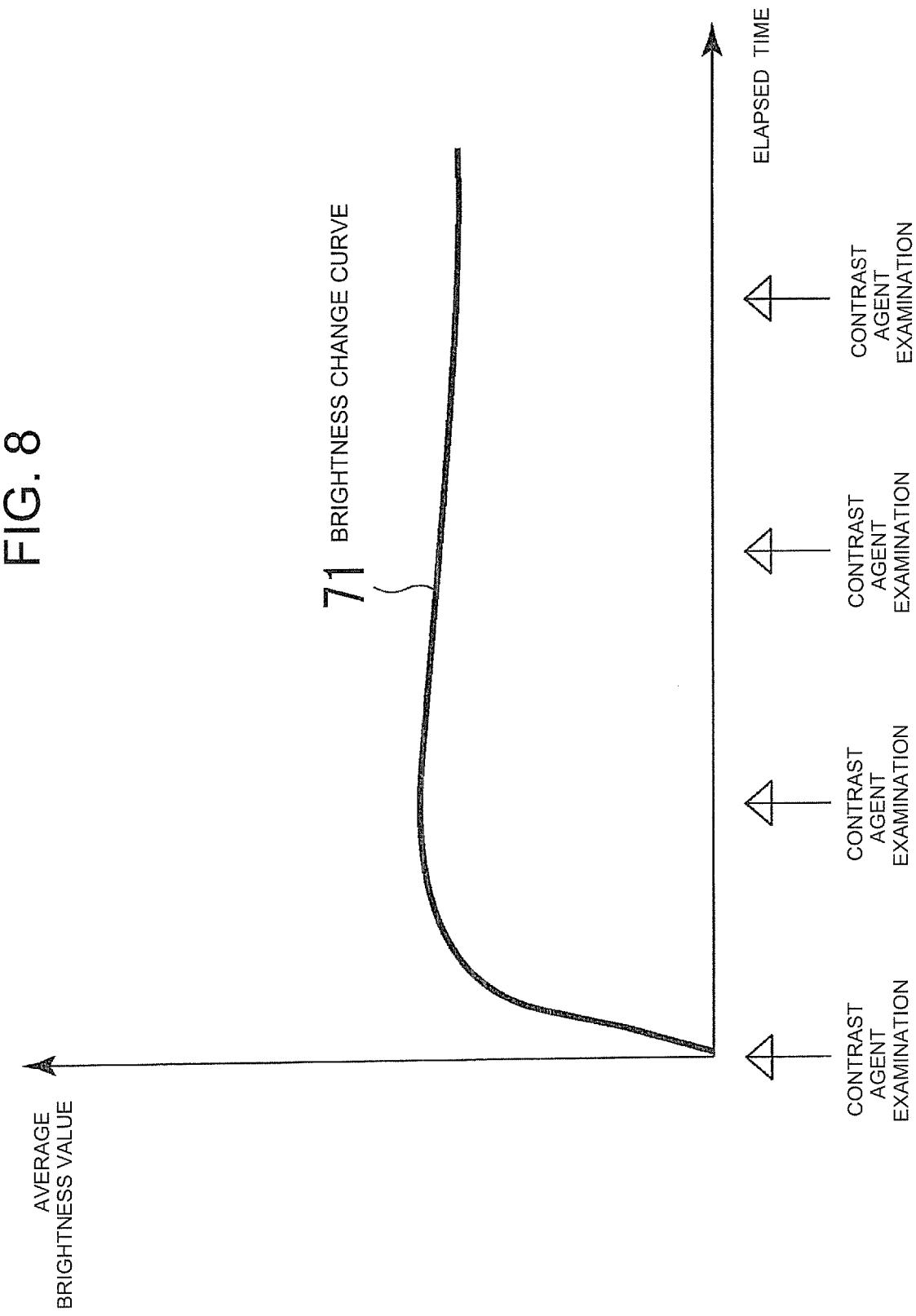
FIG. 8 is an explanatory diagram showing a brightness change curve of a subject to which a contrast agent is administered.

FIG. 8 is an explanatory diagram showing one example of a brightness change curve 71 indicated by an average brightness value of ROI 63 set to a tissue portion when a contrast agent administered to the blood permeates through the tissue portion. The horizontal axis indicates the time that elapses from the time when the contrast agent has been administered to the subject 1. The vertical axis indicates the average brightness value of ROI 63 corresponding to the region of interest set to the tissue portion. As the contrast agent in the blood reaches the region of interest of the tissue portion, the average brightness value rises and hence the brightness change curve 71 reaches the peak. After the brightness change curve 71 has reached the peak, it undergoes a transition while the peak value is being substantially maintained.

The transition of the peak value of the brightness change curve 71 results in one on which the state of the contrast agent existent in the tissue portion is reflected. When, for example, the contrast agent does not enter into the cells of the tissue portion, the contrast agent flows into the capillary blood vessels and flows out from the region of interest. As a result, the peak value of the brightness change curve 71 causes even its reduction. Incidentally, such a change in the brightness change curve 71 occurs over a period of a few minutes to a few hours and is decided by performing intermittent inspections or examinations on the subject 1. An example illustrative of examination times at which the intermittent examinations are performed at positions indicated by arrows along the horizontal axis indicating the elapsed time, is shown in FIG. 8. The contrast agent examinations are repeatedly performed at predetermined time intervals corresponding to about a few ten minutes from the administration of the contrast agent.

Referring back to FIG. 7, the operator thereafter determines whether the offset time should be inputted manually (Step S603). Here, when a treatment chamber for administering the contrast agent to the subject 1, and an inspection or examination chamber for imaging the subject 1 are located at different positions respectively, a time lag occurs between the time at which the contrast agent has been administered and the time at which the administration time timer 23 is started up. Since it is necessary to input the time lag as the offset time, the operator selects the manual input of the offset time through the manual/automatic switching key 77 of the input unit 107 (YES at Step S603). Thus, the manual time setting device 29 of the offset time setting device 24 is held in a selected state.

Here, the operator measures a time lag up to the conveying of the subject 1 to the examination chamber by himself after the administration of the contrast agent to the subject 1 and manually inputs the so-measured time information from the input unit 107 (Step S604). The time information is read into the manual time setting device 29 of the offset time setting device 24. Thereafter, the operator starts up the administration time timer 23 through the timer start key 75 of the input unit 107 (Step S605). With its start-up, the offset time setting device 24 transfers the time information of the manual time setting device 29 to the register 34 of the administration time timer 23. The administration time timer 23 reads the offset time information of the register 34 into the counter 33 and starts counting of elapsed time to which the offset time is added. The display unit 106 causes the timer display part 62 to start the display of elapsed time information of the counter 33. Incidentally, the operator is capable of manually inputting the offset time information in any case in which the difference in time occurs between the administration of the contrast agent and the start-up of the administration time timer 23.

When the examination chamber for imaging the subject 1 and the location for administering the contrast agent to the subject 1 are identical, the above time lag does not occur and hence the operator selects where the offset time information is not inputted manually (NO at Step S603). Since the offset time is automatically inputted in this case, the automatic time setting device 25 is selected. Thereafter, the operator starts up the administration time timer 23 through the timer start key 75 (Step S606) and performs an offset time setting process (Step S607).

Figure 9:
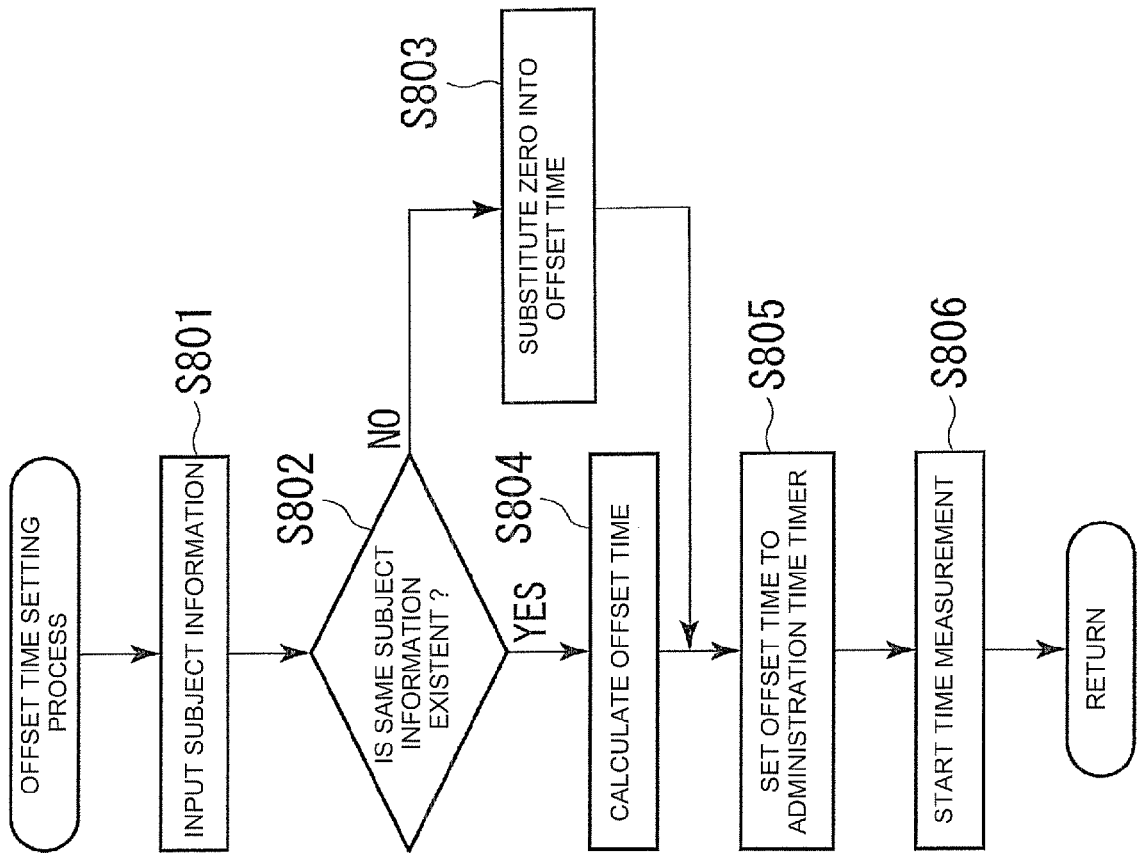
FIG. 9 is a flowchart illustrating the operation of an offset time setting process according to the embodiment.

FIG. 9 is a flowchart showing the operation of the offset time setting process. The automatic time setting device 25 inputs subject information at the execution of its start-up from the input unit 107 (Step S801) and determines whether the same subject information exists in the operation history memory unit 26 (Step S802). Since the subject 1 is subjected to the first contrast agent examination where the same subject information does not exist in the operation history memory unit 26 (NO at Step S802), the automatic time setting device 25 substitutes zero into an initial value OSTP of elapsed time calculated at the offset calculation device 28 (Step S803).

When the same subject information as the subject 1 exists in the operation history memory unit 26 (NO at Step S802), the automatic time setting device 25 reads the stop time information and the elapsed time information of the administration time timer 23 both linked to the subject information from the operation history memory unit 26 and transfers the same to the offset calculation device 28. The offset calculation device 28 calculates the initial value OSTP of the elapsed time using the above-mentioned equation, based on the stop time information and the elapsed time information, and the standard time information read from the standard time timer 22 (Step S804).

Thereafter, the offset calculation device 28 transfers offset time OSTP information indicative of an initial value to the register 34 of the administration time timer 23 (Step S805). The administration time timer 23 loads the offset time information of the register 34 to the counter 33 and thereafter starts time counting (Step S806). The display unit 106 causes the timer display part 62 to start the display of the elapsed time information of the counter 33.

Referring back to FIG. 7, the operator thereafter performs imaging for measuring the average brightness value of the regions of interest while observing the elapsed time of the administration time timer 23 on such a display screen as shown in FIG. 6 (Step S608).

Afterwards, the operator stops the count of the administration time timer 23 through the timer stop key 76 along with the end of the imaging (Step S609). Here, the administration time timer 23 and the standard time timer 22 store the elapsed time information of the counter 33 indicative of the operation history time information, and the stop time information of the standard time timer 22 in the operation history memory unit 26 simultaneously with the stop of the count (Step S610). In this storage, the operation history memory unit 26 stores the elapsed time information and the stop time information therein with being linked to the subject information at the execution of imaging. Incidentally, the elapsed time information displayed on the timer display part 62 is deleted together with the stop of the count.

Thereafter, the operator determines whether imaging is performed on the same subject 1 again after a predetermined time (Step S611). When the imaging is performed on the same subject 1 (YES at Step S611), the operator waits for the elapse of the predetermined time (Step S612). Incidentally, during the time for this waiting state, the operator is also capable of inspecting or examining another subject using the ultrasonic imaging apparatus and is able to operate the ultrasonic imaging apparatus efficiently.

Thereafter, the operator inputs the subject information of the subject 1 to the ultrasonic imaging apparatus (Step S613) after the elapse of the predetermined time (YES at Step S612), and starts the examination of the subject 1 again. Upon this examination, the operator proceeds to Step S603 and sequentially executes Steps S603 through S611.

When the imaging is not performed on the same subject 1 (NO at Step S611), the operator ends the preset or actual processing.

In the present embodiment as described above, the register 34 is provided in the administration time timer 23 and the time on which the offset time is overlaid is measured by the counter 33. Therefore, even when the intermittent examinations are performed upon the contrast agent examination over a long period of time, the count value of the administration time timer 23 can always be set as the time after the administration of the contrast agent, and a miss-free contrast agent examination can be carried out without imposing a burden on the operator.

Although, in the present embodiment, the offset time is inputted directly from the keyboard 70 of the input unit 107 when the offset time is manually inputted at Step S604 of the flowchart shown in FIG. 7, the offset time can also be calculated by providing the screen of the administration time input part 64 in the display unit 106 and using administration time information inputted from the screen thereof.

Figure 10:
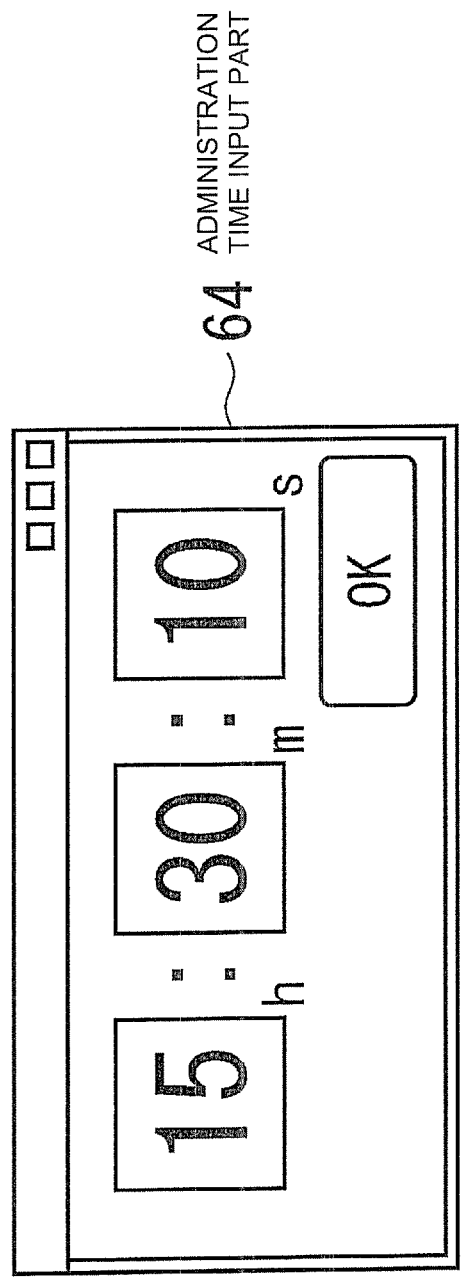
FIG. 10 is an explanatory diagram showing one example of an administration time input part displayed on the display unit.

FIG. 10 is one example of the administration time input part 64 displayed on the display unit 106. The administration time input part 64 has an input window for inputting the time at which the contrast agent is administered to the corresponding subject and inputs an administration time to the input window manually. Thereafter, the time information of the input window is transferred to, for example, the manual time setting device 29 by pressing an OK button. The manual time setting device 29 determines a difference between the administration time information and the standard time information of the standard time timer 22 and sets it as an offset time, and loads the offset time into the register 34 as an initial value of elapsed time.

Although the subject information and the operation history time information of the administration time timer 23 have been stored in the operation history memory unit 26 in the present embodiment, it is also possible to input these information to the header or the like of the acquired tomographic image information and store the same in the image memory unit 104. In this case, upon the calculation of offset time, the operation history determination device 27 retrieves the image memory unit 104 to detect the corresponding operation history time information about the administration of the contrast agent executed in the past.

Although the stop time information and the elapsed time information have been used as the operation history time information stored in the operation history memory unit 26 in the present embodiment, the start time information for starting the start-up of the administration time timer 23 can also be used in place of the stop time information.

Many widely different embodiments of the invention may be configured without departing from the spirit and the scope of the present invention. It should be understood that the present invention is not limited to the specific embodiments described in the specification, except as defined in the appended claim.

The invention claimed is:

1. An ultrasonic imaging apparatus configured to acquire tomographic image information of a subject to which a contrast agent is administered and to display the tomographic image information, said ultrasonic imaging apparatus comprising:
   a probe unit configured to acquire the tomographic image information;
   a display unit configured to display the tomographic image information;
   an administration time timer configured to start while acquisition of the tomographic image information is being performed and to measure a total time elapsed by adding an offset time to the time that elapses after the start of the administration time timer; and
   an offset time setting device configured to set the offset time within said administration time timer when said administration time timer is started, wherein the offset time is set based on a standard time at which the administration time timer is started, stop time information that indicates a standard time at which the administration time timer was previously stopped, and elapsed time information that indicates an elapsed time between an instant when the administration time timer was previously started and the standard time at which the administration time timer was previously stopped, the stop time information and the elapsed time information both linked to subject information that identifies the subject.

2. The ultrasonic imaging apparatus according to claim 1, wherein the offset time is a time that begins when the contrast agent administration is performed and ends when said administration time timer is started.

3. The ultrasonic imaging apparatus according to claim 2, further comprising a timer start key configured to start said administration time timer and a timer stop key configured to stop said administration time timer.

4. The ultrasonic imaging apparatus according to claim 1, wherein said offset time setting device comprises a manual time setting device configured to manually input offset time information indicative of the offset time.

5. The ultrasonic imaging apparatus according to claim 2, wherein said offset time setting device comprises a manual time setting device configured to manually input offset time information indicative of the offset time.

6. The ultrasonic imaging apparatus according to claim 3, wherein said offset time setting device comprises a manual time setting device configured to manually input offset time information indicative of the offset time.

7. The ultrasonic imaging apparatus according to claim 4, further comprising a contrast administration time input part configured to input contrast administration time information that includes the time when the contrast agent administration is performed.

8. The ultrasonic imaging apparatus according to claim 1, wherein said offset time setting device comprises an automatic time setting device configured to automatically input the offset time information indicative of the offset time.

9. The ultrasonic imaging apparatus according to claim 2, wherein said offset time setting device comprises an automatic time setting device configured to automatically input the offset time information indicative of the offset time.

10. The ultrasonic imaging apparatus according to claim 3, wherein said offset time setting device comprises an automatic time setting device configured to automatically input the offset time information indicative of the offset time.

11. The ultrasonic imaging apparatus according to claim 8, wherein said automatic time setting device comprises an image memory unit configured to store, when the administration time timer is stopped, the subject information, and operation history time information related to operation of said administration time timer in association with the subject information as header information of the tomographic image information along with the tomographic image information.

12. The ultrasonic imaging apparatus according to claim 8, wherein said automatic time setting device comprises an operation history memory unit configured to store, when the administration time timer is stopped, the subject information, and operation history time information related to operation of said administration time timer in association with the subject information.

13. The ultrasonic imaging apparatus according to claim 11, wherein said automatic time setting device comprises an operation history determination device coupled to the image memory unit and an operation history memory unit and configured to determine whether the subject information exists in one of said image memory unit and said operation history memory unit upon the start of said administration time timer.

14. The ultrasonic imaging apparatus according to claim 13, wherein said operation history determination device is configured to set the offset time to zero when the subject information is nonexistent in said image memory unit and said operation history memory unit.

15. The ultrasonic imaging apparatus according to claim 13, wherein said operation history determination device comprises an offset calculation device configured to calculate the offset time based on the operation history time information associated with the subject information stored in said operation history memory unit when the subject information exists in at least one of said image memory unit and said operation history memory unit.

16. The ultrasonic imaging apparatus according to claim 12, wherein the operation history time information includes any two of start time information indicative of a start time of said administration time timer, the stop time information, and the elapsed time information.

17. The ultrasonic imaging apparatus according to claim 1, wherein said offset time setting device is configured to set the offset time by adding the elapsed time to a rest time that elapses between the standard time at which the administration time timer was previously stopped and the standard time at which the administration time timer is started.

18. The ultrasonic imaging apparatus according to claim 17, wherein said display unit comprises a timer display part configured to display a standard time on a display screen.

19. The ultrasonic imaging apparatus according to claim 18, wherein said timer display part is configured to display the total time elapsed on said display screen.

20. The ultrasonic imaging apparatus according to claim 19, wherein the elapsed time is displayed on said display unit when said administration time timer is started, and is deleted from said display unit when said administration time timer is stopped.

* * * * *